(12) United States Patent
Fukushi et al.

(10) Patent No.: US 11,918,534 B2
(45) Date of Patent: Mar. 5, 2024

(54) OPTIMUM ELASTIC STRENGTH CALCULATION DEVICE, OPTIMUM ELASTIC STRENGTH CALCULATION SYSTEM, MOTION ASSISTANCE SYSTEM, OPTIMUM ELASTIC STRENGTH CALCULATION METHOD, AND OPTIMUM ELASTIC STRENGTH CALCULATION PROGRAM RECORDING MEDIUM

(71) Applicant: NEC CORPORATION, Tokyo (JP)

(72) Inventors: Kenichiro Fukushi, Tokyo (JP); Yusuke Sekiguchi, Miyagi (JP); Dai Owaki, Miyagi (JP); Keita Honda, Miyagi (JP); Shinichi Izumi, Miyagi (JP)

(73) Assignee: NEC CORPORATION, Tokyo (JP)

( * ) Notice: Subject to any disclaimer, the term of this patent is extended or adjusted under 35 U.S.C. 154(b) by 1007 days.

(21) Appl. No.: 16/753,611

(22) PCT Filed: Jul. 18, 2018

(86) PCT No.: PCT/JP2018/026906
§ 371 (c)(1),
(2) Date: Apr. 3, 2020

(87) PCT Pub. No.: WO2019/069534
PCT Pub. Date: Apr. 11, 2019

(65) Prior Publication Data
US 2020/0289356 A1   Sep. 17, 2020

(30) Foreign Application Priority Data
Oct. 5, 2017   (JP) .................. 2017-195272

(51) Int. Cl.
*A61H 3/00*      (2006.01)
*G16H 10/60*   (2018.01)
(Continued)

(52) U.S. Cl.
CPC ............... *A61H 3/00* (2013.01); *G16H 10/60* (2018.01); *G16H 20/30* (2018.01); *G16H 40/63* (2018.01);
(Continued)

(58) Field of Classification Search
CPC ............... A61H 3/00; A61H 2003/007; A61H 2201/1642; A61H 2201/165;
(Continued)

(56) References Cited

U.S. PATENT DOCUMENTS

2005/0070834 A1 * 3/2005 Herr .................... A61F 2/70
                                                          602/28
2006/0046907 A1 * 3/2006 Rastegar ............ A63B 69/0028
                                                          482/148
(Continued)

FOREIGN PATENT DOCUMENTS

JP    4156909 B2    9/2008
JP    3169692 U     8/2011
(Continued)

OTHER PUBLICATIONS

Written Opinion of the International Searching Authority dated Oct. 9, 2018 in International Application. No. PCT/JP2018/026906.
(Continued)

*Primary Examiner* — Quang D Thanh
(74) *Attorney, Agent, or Firm* — Sughrue Mion, PLLC

(57) ABSTRACT

The present invention facilitates adjustment of the strength of an elastic orthotic that assists the movement of an orthotics user by whom the elastic orthotic is worn. This calculation device for calculating the optimum elastic strength of an elastic includes a storage unit in which elastic strength or kinematic properties established through experiments in which a plurality of people wear elastic orthotics are stored in advance, and a mathematical optimization
(Continued)

processing unit that calculates the optimal elastic strength on the basis of a prescribed evaluation index on the basis of the kinematic limitations of an orthotics user and the elastic strength or kinetic properties.

11 Claims, 4 Drawing Sheets

(51) Int. Cl.
*G16H 20/30* (2018.01)
*G16H 40/63* (2018.01)
*G16H 50/30* (2018.01)

(52) U.S. Cl.
CPC ....... *G16H 50/30* (2018.01); *A61H 2003/007* (2013.01); *A61H 2201/1642* (2013.01); *A61H 2201/165* (2013.01); *A61H 2201/5007* (2013.01); *A61H 2201/5043* (2013.01); *A61H 2201/5069* (2013.01); *A61H 2201/5097* (2013.01); *A61H 2205/106* (2013.01); *A61H 2205/108* (2013.01)

(58) Field of Classification Search
CPC .... A61H 2201/5007; A61H 2201/5043; A61H 2201/5069; A61H 2201/5097; A61H 2205/106; A61H 2205/108; A61H 1/00; G16H 10/60; G16H 20/30; G16H 40/63; G16H 50/30; A61F 2/68; A63B 21/02; A63B 24/00

See application file for complete search history.

(56) References Cited

U.S. PATENT DOCUMENTS

| | | |
|---|---|---|
| 2009/0024061 A1 | 1/2009 | Ueda et al. |
| 2012/0108397 A1 | 5/2012 | Tsai |
| 2012/0259429 A1* | 10/2012 | Han .................. A61F 5/0127 623/24 |
| 2013/0268256 A1 | 10/2013 | Dariush |
| 2016/0262969 A1* | 9/2016 | Ohta ..................... A61H 3/00 |
| 2017/0119615 A1 | 5/2017 | Shim et al. |

FOREIGN PATENT DOCUMENTS

| | | |
|---|---|---|
| JP | 2015-523544 A | 8/2015 |
| JP | 2016-182666 A | 10/2016 |
| WO | 2006/092872 A1 | 9/2006 |
| WO | 2016/006432 A1 | 1/2016 |
| WO | 2016/024368 A1 | 2/2016 |

OTHER PUBLICATIONS

International Search Report for PCT/JP2018/026906 dated Oct. 9, 2018 [PCT/ISA/210].

* cited by examiner

OPTIMUM ELASTIC STRENGTH CALCULATION DEVICE, OPTIMUM ELASTIC STRENGTH CALCULATION SYSTEM, MOTION ASSISTANCE SYSTEM, OPTIMUM ELASTIC STRENGTH CALCULATION METHOD, AND OPTIMUM ELASTIC STRENGTH CALCULATION PROGRAM RECORDING MEDIUM

CROSS REFERENCE TO RELATED APPLICATIONS

This application is a National Stage of International Application No. PCT/JP2018/026906 filed Jul. 18, 2018, claiming priority based on Japanese Patent Application No. 2017-195272 filed Oct. 5, 2017, the disclosure of which are incorporated herein by reference in their entirety.

TECHNICAL FIELD

This invention relates to an optimum elastic strength calculation device, an optimum elastic strength calculation system, a motion assistance system, an optimum elastic strength calculation method, and an optimum elastic strength calculation program recording medium.

BACKGROUND ART

Various proposals have been made as regards a device which is worn on a body of an orthotics user to assist a motion (e.g. walking motion) of the orthotics user and, in particular, an elastic orthotic device for assisting the motion by using a force generated by an elastic body.

For instance, Patent Literature 1 describes a walking assistance machine for assisting rotation of a hip joint using a force generated by a compression spring as an elastic body.

In addition, Patent Literature 2 describes a short leg brace for assisting rotation of an ankle joint using a force generated by a coil spring as an elastic body.

Various techniques related to this invention are also known.

For instance, Patent Literature 3 discloses a method of determining a pose of a virtual human body within a vehicle occupant packaging design based on a set of constraints. In Patent Literature 3, the computer system receives a vehicle occupant packaging design (design) to be evaluated, parameters describing an articulated model of the virtual human body, a set of constraints limiting the motion of the virtual human body within the design, and one or more physical tasks (operational tasks) to be carried out by the virtual human body within the design. The pose determination system is configured to determine the pose of the virtual human body while adhering to the set of constrains imposed on the virtual human body's motion. The initial posture is determined using a closed form multi objective optimization (MOO) technique. This technique incorporates a differential kinematic model to determine the pose. The technique is analytically derived and runs in real-time.

In addition, Patent Literature 4 discloses a technique of calculating a driving force of a muscle force assisting device. In Patent Literature 4, the muscle force assisting device is worn by a living body (human) having bones with joints and muscles. Each of driving sections is fixed to the bones of the living body (human) across the joint. Each driving section is, for example, an actuator having a bar shape that can extend and contact or an artificial pneumatic rubber muscle with elastic fiber composite. A driving force control section drives each driving section based on the driving force calculated by a driving force calculating device. A muscle force calculating section of the driving force calculating device optimizes muscle forces of the respective muscles so that an evaluation function of optimization calculation proposed by Crowninshield has the minimum value. A constraint condition may be added in the optimization using the evaluation function.

Furthermore, Patent Literature 5 discloses a treadle-operated muscle stretching machine which can adjust strength and an angle while stretching muscles. In Patent Literature 5, an elastic rope fixing rod is pivotably attached to the center of a core frame whereas an elastic rope fixing pin disposed at an upper end thereof fixes one end of an elastic rope. The elastic rope fixing rod is fixed to the core frame via an angle adjustment tool. It is possible to adjust resistance strength of the elastic rope by the angle adjustment tool. By the angle adjustment tool, the elastic rope fixing rod can adjust a tensile force of the elastic rope and, in turn, can adjust resistance of a treadle. It is possible to adjust the angle while stretching the muscles.

CITATION LIST

Patent Literature

PTL 1: WO 2016/024368 A1
PTL 2: JP 4156909 B
PTL 3: JP 2015-523544 A
PTL 4: WO 2006/092872 A1
PLT 5: JP 3169692 U

SUMMARY OF INVENTION

Technical Problem

The devices disclosed in the Patent Literature 1 and Patent Literature 2 mentioned above comprise an adjustment screw for manually adjusting elastic strength, and the elastic strength must be appropriately set with due consideration of various states of the orthotics user, such as an individual difference in gait, a muscle weakness condition, and a paralysis state of each individual orthotics user. Herein, the "gait" means a manner of body motion during walking.

However, the adjustment thereof is not easy. For instance, it is assumed that the elastic strength of the elastic orthotic device for assisting flexion movement of the hip joint is increased. In this event, forward swinging of a thigh is more strongly assisted in a swing phase. However, on the other hand, normal walking may be disturbed because a stretching angle of the hip joint decreases due to a resistance force for saving elastic energy from mid stance to late stance and because a load on the joint becomes larger.

Furthermore, adjustment is difficult also because an assistance effect of the orthotic device is not limited to a part to be directly assisted. For instance, it is known that, when an elastic orthotic device in an ankle joint is worn by a hemiplegia patient, the stretching angle of the hip joint also changes. Therefore, the walking state may rather become worse if appropriate elastic strength is not set. Thus, it is difficult to easily carry out strength adjustment of the elastic orthotic device.

In addition, any of the above-mentioned Patent Literatures 3 to 5 does not disclose a technique of automatically adjusting the strength of the elastic orthotic device.

Specifically, Patent Literature 3 merely discloses the technique of determining the pose of the virtual human body based on the set of constraints. Patent Literature 4 merely discloses the technique of optimizing muscle forces of the respective muscles so that the predetermined evaluation function has the minimum value in order to calculate the driving force of the driving sections fixed to the bones of the living body across the joint. Patent Literature 5 merely discloses the treadle-operated muscle stretching machine which can manually adjust the tensile force of the elastic rope by using the angle adjustment tool.

It is an object of this invention to provide an optimum elastic strength calculation device, an optimum elastic strength calculation system, a motion assistance system, an optimum elastic strength calculation method, and an optimum elastic strength calculation program recording medium, which resolve the above-mentioned problems and which are capable of easily carrying out strength adjustment of an elastic orthotic device.

Solution to Problem

An optimum elastic strength calculation device according to an example embodiment of the present invention comprises a storage unit configured to preliminarily store an elastic strength and kinematic property obtained through experiments in a state where an elastic orthotic device for assisting an action of an orthotics user is worn on bodies of a plurality of persons; and an optimization problem processing unit configured to calculate an optimum elastic strength of the elastic orthotic device based on a predetermined evaluation index using a kinematic constraint condition of the orthotics user and the elastic strength and kinematic property, An optimum elastic strength calculation system of the present invention comprises an input device configured to input a kinematic constraint condition of an orthotics user; the above-mentioned optimum elastic strength calculation device; and a display device configured to output the optimum elastic strength.

Furthermore, a motion assistance system of the present invention comprises an elastic orthotics device which is configured to be worn on a body of an orthotics user to assist an action of the orthotics user; an input device configured to input a kinematic constraint condition of the orthotics user; the above-mentioned optimum elastic strength calculation device; and an adjustment device configured to adjust, in response to the optimum elastic strength, an elastic strength of the elastic orthotic device.

An optimum elastic strength calculation method of the present invention comprises preliminarily storing, in a storage unit, an elastic strength and kinematic property which is obtained through experiments in a state where an elastic orthotic device for assisting an action of an orthotics user is worn on bodies of a plurality of people; and calculating, by an optimization problem processing unit, an optimum elastic strength of the elastic orthotic device based on a predetermined evaluation index using a kinematic constraint condition of the orthotics user and the elastic strength and kinematic property.

An optimum elastic strength calculation program recording medium of the present invention is for recording an optimum elastic strength calculation program to cause a computer to calculate an optimum elastic strength of an elastic orthotic device which is worn on a body of an orthotics user to assist an action of the orthotics user, wherein the optimum elastic strength calculation program causes the computer to execute a step of preliminarily storing, in a storage unit, an elastic strength and kinematic property which is obtained through experiments in a state where the elastic orthotic device for assisting the action of the orthotics user is worn on bodies of a plurality of people; and an optimization problem processing step of calculating the optimum elastic strength of the elastic orthotic device based on a predetermined evaluation index using a kinematic constraint condition of the orthotics user and the elastic strength and kinematic property.

An optimum elastic strength calculation device according to another example embodiment of the present invention comprises a storage unit configured to preliminarily store an elastic strength and kinematic property obtained through experiments in a state where an elastic orthotic device for assisting an action of an orthotics user is worn on bodies of a plurality of people; a conversion unit configured to convert mobility evaluation information of the orthotics user into a kinematic constraint condition; and an optimization problem processing unit configured to calculate an optimum elastic strength of the elastic orthotic device based on a predetermined evaluation index using the kinematic constraint condition and the elastic strength and kinematic property.

An optimum elastic strength calculation system of the present invention comprises an input device configured to input mobility evaluation information of an orthotics user; the above-mentioned optimum elastic strength calculation device; and a display device configured to output the optimum elastic strength.

Furthermore, an exercise assistance system of the present invention comprises an elastic orthotic device which is configured to be worn on a body of an orthotics user to assist an action of the orthotics user; an input device configured to input mobility evaluation information of the orthotics user; the above-mentioned optimum elastic strength calculation device; and an adjustment device configured to adjust, in response to the optimum elastic strength, an elastic strength of the elastic orthotic device.

An optimum elastic strength calculation method of the present invention comprises preliminarily storing, in a storage unit, an elastic strength and kinematic property which is obtained through experiments in a state where an elastic orthotic device for assisting an action of an orthotics user is worn on bodies of a plurality of people; converting, by a conversion unit, mobility evaluation information of the orthotics user into a kinematic constraint condition; and calculating, by an optimization problem processing unit, an optimum elastic strength of the elastic orthotic device based on a predetermined evaluation index using the kinematic constraint condition and the elastic strength and kinematic property.

An optimum elastic strength calculation program recording medium of the present invention is for recording an optimum elastic strength calculation program to cause a computer to calculate an optimum elastic strength of an elastic orthotic device which is worn on a body of an orthotics user to assist an action of the orthotics user, wherein the optimum elastic strength calculation program causes the computer to execute a step of preliminarily storing, in a storage unit, an elastic strength and kinematic property which is obtained through experiments in a state where the elastic orthotic device for assisting the action of the orthotics user is worn on bodies of a plurality of people; a conversion step of converting mobility evaluation information of the orthotics user into a kinematic constraint condition; and an optimization problem processing step of calculating the optimum elastic strength of the elastic orthotic device based on a predetermined evaluation index using the kinematic constraint condition and the elastic strength and kinematic property.

Advantageous Effect of Invention

According to this invention, it is possible to easily carry out strength adjustment of an elastic orthotic device.

DESCRIPTION OF EMBODIMENTS

First Example Embodiment

Next, a first example embodiment of the present invention will be described in detail with reference to the drawings.

Figure 1:
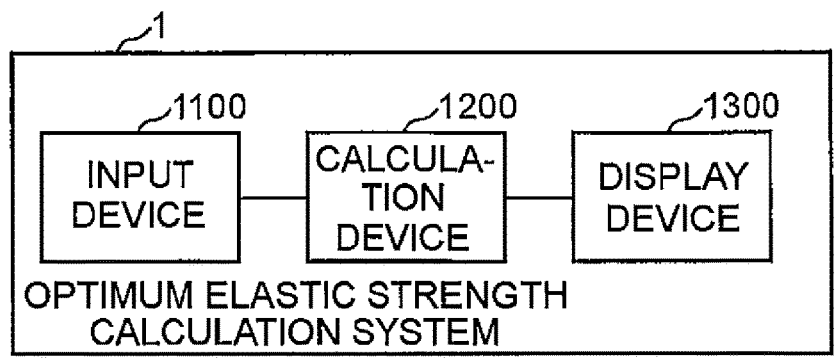
FIG. 1 is a block diagram for illustrating an example of a configuration of an optimum elastic strength calculation system according to a first example embodiment of the present invention.

FIG. 1 is a block diagram for illustrating an example of a configuration of an optimum elastic strength calculation system 1 according to a first example embodiment of the present invention. As illustrated in FIG. 1, the optimum elastic strength calculation system 1 comprises an input device 1100, a calculation device 1200, and a display device 1300.

A connection method for the respective devices may be, for example, wire connection using a LAN (Local Area Network) cable, a USB (Universal Serial Bus) cable or the like, or may be wireless connection using Bluetooth (registered trademark), WiFi, or the like, without being limited thereto.

The input device 1100 comprises a user interface for inputting a kinematic constraint condition of an orthotics user. Herein, the "kinematic constraint condition" is a kinematic condition to be satisfied by a pedestrian during an action such as during walking or during running and includes a limiting scope for a range of joint motion, an upper limit of a joint moment, an upper limit of a muscle activity amount, and so on. The input device 1100 supplies the input kinematic constraint condition to the calculation device 1200.

The calculation device 1200 receives the kinematic constraint condition from the input device 1100. The calculation device 1200 calculates an optimum elastic strength using the received kinematic constraint condition, as will later be described. A specific functional configuration of the calculation device 1200 will be described after changing the reference figure.

The display device 1300 is means for displaying the optimum elastic strength which is a processed result of the calculation device 1200.

Configuration of the Calculation Device 1200

Figure 2:
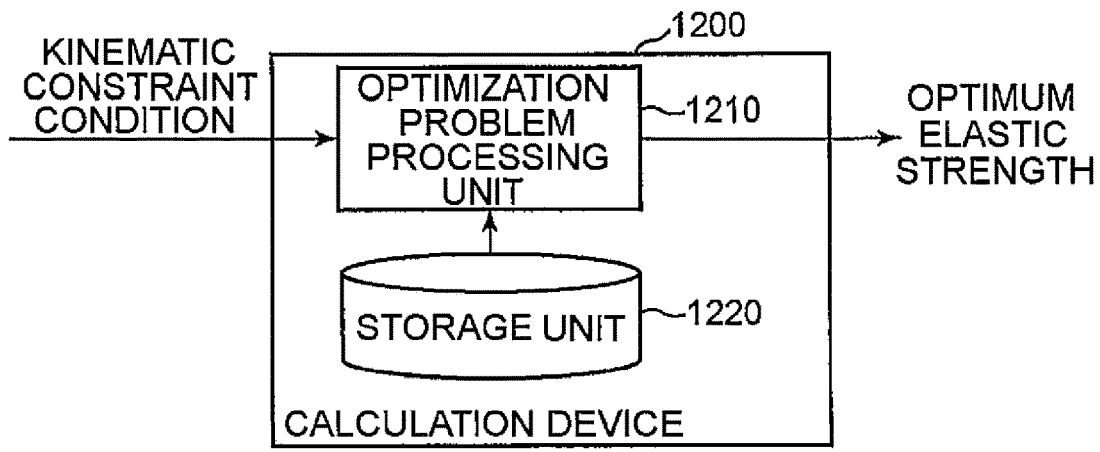
FIG. 2 is a block diagram for illustrating an example of a configuration of a calculation device according to the first example embodiment of the present invention.

Next referring to FIG. 2, the calculation device 1200 of the first example embodiment will be described. As illustrated in FIG. 2, the calculation device 1200 comprises an optimization problem processing unit 1210 and a storage unit 1220.

The calculation device 1200 is a device which is worn on a body of the orthotics user to calculate the optimum elastic strength of an elastic orthotic device for assisting an action of the orthotics user.

The optimization problem processing unit 1210 receives the kinematic constraint condition and carries out processing, which will later be described, to produce the optimum elastic strength:

$$\hat{x} \qquad \text{[Math. 1]}$$

In the first example embodiment, description will be made as regards a case where the kinematic constraint condition is the following (A) and (B):

(A) Limit values of a maximum bending angle, a maximum extension angle, and a maximum joint moment in each of a hip joint, a knee joint, and an ankle joint; and (B) Limit values of a maximum muscle activity amount in each of gluteus maximus, rectus femoris, medial great muscle, semimembranosus, biceps femoris muscle, soleus muscle, gastrocnemius muscle, and anterior tibialis muscle.

It is to be noted that the kinematic constraint condition is not limited to the limit values of the maximum bending angle, the maximum extension angle, the maximum joint moment, and the maximum muscle activity amount mentioned above. For instance, it is conceivable that a limit value of a range of joint motion which is defined by a sum of the maximum extension angle and the maximum bending angle, a limit value of a joint angular speed representing a rotational speed of the joint, a limit value of an extension amount of the muscle, and a tensile load of a ligament are used as the kinematic constraint condition.

Furthermore, the joints and the muscles are not limited to the above-mentioned parts, and may appropriately be selected depending on an assistance target part for the elastic orthotic device for carrying out the strength adjustment. For instance, it is conceivable to select, as the joints in a case of carrying out the strength adjustment of the elastic orthotic device for assisting a movement of an upper limb, a sternoclavicular joint, an acromioclavicular joint, a scapulothoracic joint, a scapulohumeral joint, a humeroulnar joint, a humeroradial joint, and distal and proximal radioulnar joints. In addition, it is conceivable to select a lumber facet and a sacroiliac joint in a case of carrying out the strength adjustment of the elastic orthotic device for assisting a movement of a lower back.

The optimum elastic strength:

$$\hat{x} \quad \text{[Math. 2]}$$

is a solution of a constrained optimization problem of the following expression (Math. 3):

$$
\begin{aligned}
\max \quad & v(x), \ x = [x_1, x_2, \ldots, x_N] \\
\text{s.t.} \quad & \theta_l(x) \leq \overline{\theta}_l && l = \{\text{hip joint, knee joint, ankle joint}\} \\
& \phi_l(x) \leq \overline{\phi}_l && m = \{\text{gluteus maximus, rectus femoris,} \\
& \tau_l(x) \leq \overline{\tau}_l && \text{medial great muscle, semimembranosus,} \\
& MVC_m(x) \leq \overline{MVC_m} && \text{biceps femoris muscle, soleus muscle,} \\
& && \text{gastrocnemius muscle, anterior tibialis} \\
& && \text{muscle}\}
\end{aligned}
\quad \text{[Math. 3]}
$$

Herein, $x_i$ is an elastic strength of an i-th elastic orthotic device. $v(x)$ is a predictive value of a walking speed in a case where the elastic strength x of each elastic orthotic device is given. The predictive value of the walking speed is calculated by means of machine learning or a statistical method (e.g. an average, a median) on the basis of leaning data collected by preliminarily carrying out, for a sufficient number of people, experiments for measuring the walking speeds when the elastic orthotic device with the elastic strength set to x is worn.

In addition, variables in the above Math. 3 represent the following Math. 4 and Math. 5:

[Math. 4]
  $\overline{\theta}_l$ is a limit value of a maximum bending angle of a joint 1.
  $\overline{\phi}_l$ is a limit value of a maximum extension angle of the joint 1.
  $\overline{\tau}_l$ is a limit value of a maximum joint movement of the joint 1.
  $\overline{MVC_m}$ is a limit value of a maximum muscle activity amount of a muscle m.

[Math. 5]
  $\theta_l(x)$ is a predictive value of a maximum bending angle of a joint 1 when the elastic strength is set to x.
  $\phi_l(x)$ is a predictive value of a maximum extension angle of the joint 1 when the elastic strength if set of x.
  $\tau_l(x)$ is a predictive value of a maximum joint movement of the joint 1 when the elastic strength is set to x.
  $MVC_m(x)$ is a predictive value of a maximum muscle activity amount of a muscle m when the elastic strength if set to x.

In the manner similar to the walking speed v, the predictive values are calculated by means of the machine learning or the statistical method (e.g. an average, a median) on the basis of leaning data collected by preliminarily carrying out, for the sufficient number of people, experiments for measuring the maximum bending angle, the maximum extension angle, the maximum joint moment, and the maximum muscle activity amount when the elastic orthotic device with the elastic strength set to x is worn.

In the foregoing, formularization is made, as one example of optimization, on the basis of an evaluation index (first index) for maximizing the walking speed v of the orthotics user. However, this is not limited to maximization of the walking speed. For instance, in a case of rehabilitation for the purpose of improvement of a range of joint motion, an evaluation index (second index) is conceivable which is for maximizing the range of joint motion that is defined as a sum of the maximum bending angle and the maximum extension angle of the joint. In a case of emphasizing minimization of the load of the joint, it is conceivable to use an evaluation index (third index) for minimizing the maximum joint moment. Furthermore, a weighted average value of a plurality of evaluation indexes (the first through the third indexes) illustrated above may be used as an evaluation index (a fourth index). Thus, the evaluation index for optimization is appropriately set in accordance with a purpose of motion assistance and circumstances such as a progress stage of rehabilitation.

The storage unit 1220 stores an elastic strength and kinematic property. Herein, the "elastic strength and kinematic property" comprises a predictive value $v(x)$ of the walking speed, a predictive value $\theta_1(x)$ of the maximum bending angle of the joint 1, a predictive value $\phi_1(x)$ of the maximum extension angle of the joint 1, a predictive value $\tau_1(x)$ of the maximum joint moment of the joint 1, and a predictive value $MVC_m(x)$ of the maximum muscle activity amount of the muscle m which are calculated on the basis of learning data collected by wearing, on a sufficient number of the plurality of people, the elastic orthotic device for assisting the action of the orthotics user as mentioned above.

The optimization problem processing unit 1210 calculates the above-mentioned optimum elastic strength based on the above-mentioned predetermined evaluation index using the above-mentioned kinematic constraint condition and the above-mentioned elastic strength and kinematic property.

Explanation of Operation

Next, an operation of the optimum elastic strength calculation system 1 according to the first example embodiment will be described with reference to the drawings.

Figure 3:
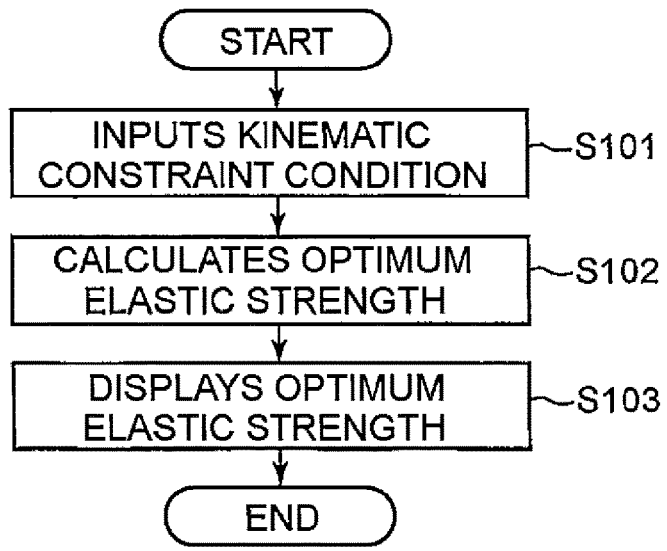
FIG. 3 is a flow chart for representing an example of an operation of the optimum elastic strength calculation system according to the first example embodiment of the present invention.

FIG. 3 is a flow chart for representing an example of the operation of the optimum elastic strength calculation system 1 according to this example embodiment.

First, the input device 1100 inputs the kinematic constraint condition (Step S101). Then, the input device 1100 supplies the input kinematic constraint condition to the calculation device 1200.

The calculation device 1200 receives the kinematic constraint condition from the input device 1100. The calculation device 1200 calculates the optimum elastic strength based on the above-mentioned predetermined evaluation index using the received kinematic constraint condition and the above-mentioned elastic strength and kinematic property (Step S102). The calculation device 1200 supplies the calculated optimum elastic strength to the display device 1300.

The display device 1300 displays the optimum elastic strength which is a processed result of the calculation device 1200 (Step S103).

In this manner, according to this first example embodiment, it is possible to easily carry out the strength adjustment of the elastic orthotic device by calculating the optimum elastic strength.

It is to be noted that each part of the calculation device 1200 may be implemented by using a combination of hardware and software. In a form in which the hardware and the software are combined, the respective parts are implemented as various kinds of means by developing an optimum elastic strength calculation program in a RAM (random access memory) and making hardware such as a control unit (a CPU (central processing unit)) operate based on the optimum elastic strength calculation program. The optimum elastic strength calculation program may be recorded in a recording medium to be distributed. The optimum elastic strength calculation program recorded in the recording medium is read into a memory via a wire, wirelessly, or via the recording medium itself to operate the control unit and so on. By way of example, the recording medium may be an optical disc, a magnetic disk, a semiconductor memory device, a hard disk, or the like.

Explaining the above-mentioned first example embodiment with a different expression, it is possible to implement the first example embodiment by making a computer to be operated as the calculation device 1200 act as the optimization problem processing unit 1210 and the storage unit 1220 according to the optimum elastic strength calculation program developed in the RAM.

Second Example Embodiment

Next, a second example embodiment of the present invention will be described with reference to the drawings.

It is to be noted that a motion assistance system according to this second example embodiment may assist a movement of a lower limb, such as walking, of the orthotics user or may assist a movement of an upper limb or a lower back such as lifting-up of an article, without being limited thereto.

In the following explanation, description will be made as regards a case of assisting a walking motion by way of example. Accordingly, in the following explanation, it is assumed that the elastic orthotic devices fitted to the lower limb, especially, to a hip joint and an ankle joint are used. As described above, however, this second example embodiment is not limited to the walking motion and the lower limb.

Explanation of Configuration

Figure 4:
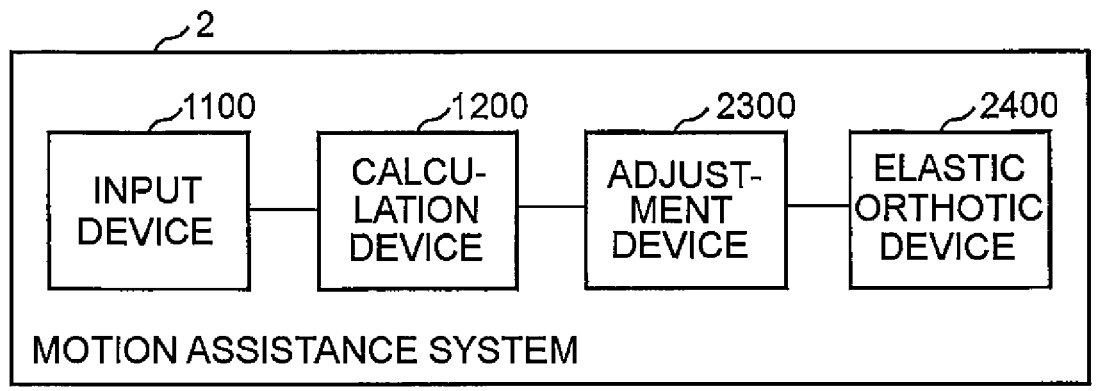
FIG. 4 is a block diagram for illustrating an example of a configuration of a motion assistance system according to a second example embodiment of the present invention.

FIG. 4 is a block diagram for illustrating an example of a configuration of a motion assistance system 2 according to the second example embodiment in the present invention. As illustrated in FIG. 4, the motion assistance system 2 comprises the input device 1100, the calculation device 1200, an adjustment device 2300, and the elastic orthotic device 2400.

The input device 1100 and the calculation device 1200 carry out operations same as those of the optimum elastic strength calculation system 1 illustrated in FIG. 1.

The adjustment device 2300 receives the optimum elastic strength from the calculation device 1200. The adjustment device 2300 adjusts elastic strength by controlling a clamping force of an elastic body in the elastic orthotic device 2400 so that the elastic strength of the elastic orthotic device 2400 coincides with the received optimum elastic strength.

The elastic orthotic device 2400 is worn on a body of the orthotics user. Then, the elastic orthotic device 2400 generates a force or a torque using the elastic body such as a spring or a rubber to assist walking of a subject. The elastic strength of the elastic orthotic device 2400 is adjusted by the above-mentioned adjustment device 2300.

Figure 5:
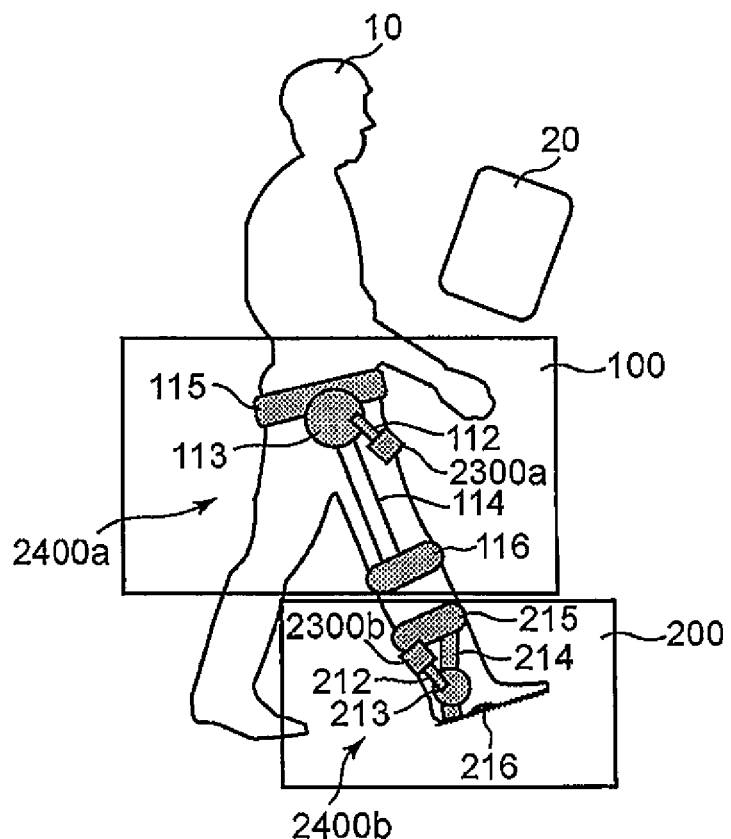
FIG. 5 is a view for illustrating an example of an external appearance of the motion assistance system according to the second example embodiment of the present invention.

FIG. 5 is a view for illustrating an example of an external appearance of the motion assistance system 2 according to this second example embodiment. The motion assistance system 2 illustrated in FIG. 5 comprises a terminal 20, a first motion assistance device 100, and a second motion assistance device 200.

The terminal 20 comprises the input device 1100 and the calculation device 1200. The terminal 20 inputs the kinematic constraint condition through an interface such as a keyboard or a touch-panel and supplies the optimum elastic strength to the adjustment device 2300. The terminal 20 and the adjustment device 2300 are connected via a wire or wirelessly. A person imputing the kinematic constraint condition to the terminal 20 is not limited to an orthotics user 10, and a doctor or a physical therapist may input. In addition, the interface is not limited to the keyboard or the touch-panel. For example, data of the kinematic constraint condition may be acquired from a remote place through the Internet connection.

The first motion assistance device 100 comprises a first adjustment device 2300a and a first elastic orthotic device 2400a.

The first elastic orthotic device 2400a comprises a first elastic body holding unit 112, a first assistance unit 113, a first shaft 114, a waist belt 115, and a knee belt 116.

The first elastic body holding unit 112 internally holds an elastic body (spring, rubber, or the like) for generating a first motion assistance force. The first assistance unit 113 is disposed at a predetermined position on a lateral side of a greater trochanter of the orthotics user 10 in order to assist rotation of the hip joint of the orthotics user 10 by using the above-mentioned first motion assistance force as a motive power. It is to be noted that the greater trochanter is a projecting part which projects outside from a proximal end of a thighbone. The waist belt 115 secures the first motion assistance device 100 to a lower back of the orthotics user 10. The first shaft 114 transmits the first motion assistance force generated by the first assistance unit 113 to an upper part of the knee or a lower part of the knee. The first shaft 114 rotates around the first assistance unit 113 as a center. That is, the first shaft 114 corresponds to an external skeleton of the thigh of the orthotics user 10. The knee belt 116 transmits the first motion assistance force of the first assistance unit 113 to the upper part of the knee or the lower part of the knee. Accordingly, the knee belt 116 is provided at a distal end of the first shaft 114.

The first adjustment device 2300a is fitted to a tip of the first elastic body holding unit 112 in FIG. 5 and adjusts the elastic strength of the first elastic orthotic device 2400a by adjusting the clamping force of the elastic body inside the first elastic body holding unit 112.

The second motion assistance device 200 comprises a second adjustment device 2300b and a second elastic orthotic device 2400b.

The second elastic orthotic device 2400b comprises a second elastic body holding unit 212, a second assistance unit 213, a second shaft 214, a shank belt 215, and a sole plate 216.

The second elastic body holding unit 212 internally holds an elastic body (spring, rubber, or the like) for generating a second motion assistance force. The second assistance unit 213 is disposed at a predetermined position on a lateral side of the ankle joint of the orthotics user 10 in order to assist rotation of the ankle joint of the orthotics user 10 by using the above-mentioned second motion assistance force as a motive power. The second shaft 214 rotates around the second assistance unit 213 as a center. That is, the second shaft 214 corresponds to an external skeleton of a lower thigh of the orthotics user 10. The shank belt 215 and the sole plate 216 serve to fasten the second motion assistance device 220 to a shank region and a foot region, respectively. The sole plate 216 transmits the second motion assistance force of the second assistance unit 213 to the foot region.

The second adjustment device 2300b is fitted to a tip of the second elastic body holding unit 212 in FIG. 5 and adjusts the elastic strength of the second elastic orthotic device 2400b by adjusting the clamping force of the elastic body inside the second elastic body holding unit 212.

A method of adjusting the clamping force of the elastic body by the first and the second adjustment devices 2300a and 2300b is not especially limited. For instance, as shown in FIG. 6, a mechanism for controlling the clamping force of the elastic body of the elastic orthotic device 2400 by means of a servomotor is conceivable.

Figure 6:
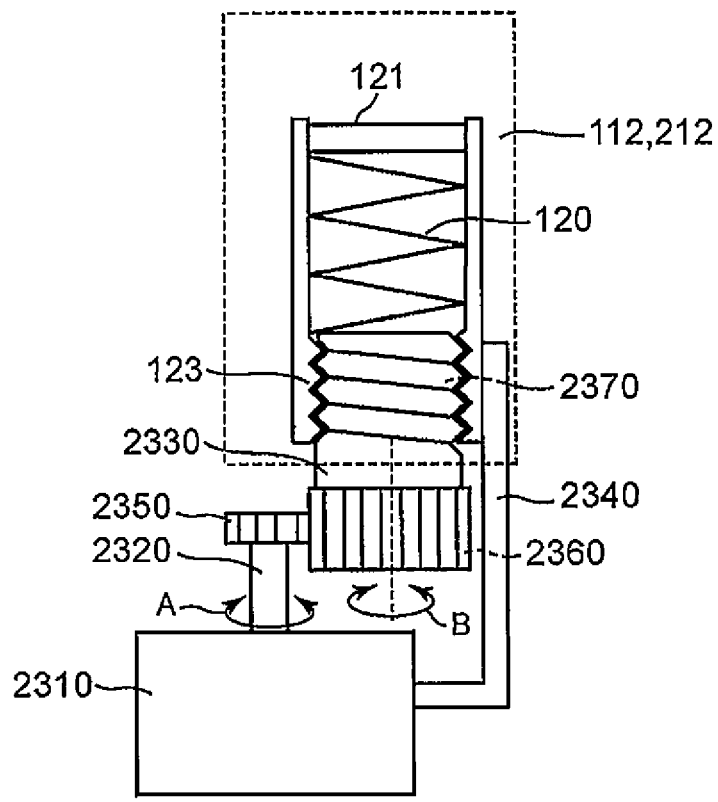
FIG. 6 is a block diagram for illustrating an example of a configuration of an elastic body holding unit and an adjustment device in an elastic orthotic device according to the second example embodiment of the present invention.

FIG. 6 is a cross-sectional view of the first and the second elastic body holding units 112, 212 and the first and the second adjustment devices 2300a, 2300b as seen from a direction of FIG. 5.

As the elastic body, a spring 120 is held in the first and the second elastic body holding units 112 and 212. A pressing force generated by the spring is applied to a pressing force reception unit 121 and is transmitted to the first and the second assistance units 113 and 213. The first and the second adjustment devices 2300a and 2300b comprise a servomotor 2310, a shaft 2320, a shaft 2330, and a fixing member 2340.

The fixing member 2340 fixes the servomotor 2310 to the first and the second elastic body holding units 112 and 212. The servomotor 2310 generates a force for rotating the shaft 2320 in a direction of an arrow A in the figure. A gear 2350 is fitted to a tip of the shaft 2320 on the side opposite from the servomotor 2310 to transmit a rotational force of the servomotor 2310 to the shaft 2330. A tip of the shaft 2330 on the side toward the servomotor 2310 is formed into a gear 2360 which rotates, in response to the rotational force from the shaft 2320, in a direction of an arrow B in the figure. Another tip of the shaft 2330 on the side toward the elastic body 120 and a tip of the first and the second elastic body holding units 112 and 212 on the side toward the shaft 2330 are formed into a male screw 2370 and a female screw 123, respectively, which are fitted with each other.

By rotating the shaft 2330, a length of the shaft 2330, that is inserted into the first and the second elastic body holding units 112 and 212, changes so as to adjust the clamping force of the elastic body (spring) 120. It is desired that a length of the gear 2360 of the shaft 2330 in a direction of a rotation axis is sufficiently long in view of a positional change caused by insertion of the shaft 2330 into the first and the second elastic body holding units 112 and 212.

Explanation of Operation

Next, an operation of the motion assistance system 2 according to the second example embodiment will be described with reference to the drawings.

Figure 7:
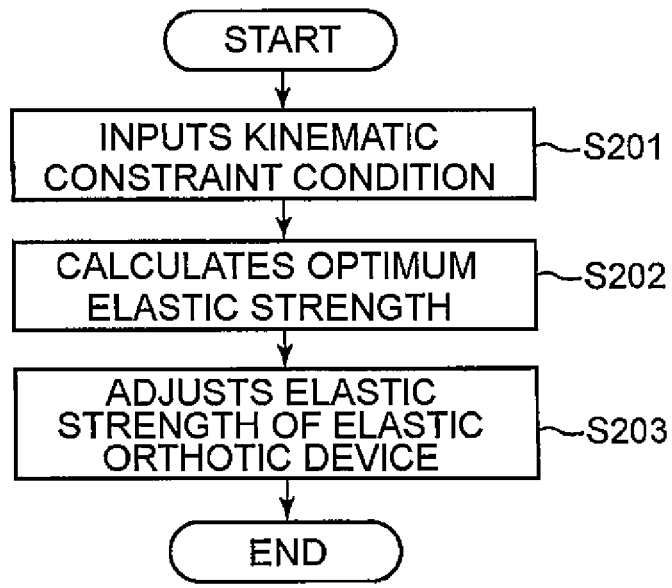
FIG. 7 is a flow chart for representing an example of an operation of the motion assistance system according to the second example embodiment of the present invention.

FIG. 7 is a flow chart for representing an example of the operation of the motion assistance system 2 according the second example embodiment.

First, the input device 1100 inputs the kinematic constraint condition (Step S201). Then, the input device 1100 supplies the input kinematic constraint condition to the calculation device 1200.

The calculation device 1200 receives the kinematic constraint condition from the input device 1100. The calculation device 1200 calculates the optimum elastic strength using the received kinematic constraint condition in the manner described above (Step S202). The calculation device 1200 supplies the calculated optimum elastic strength to the adjustment device 2300.

The adjustment device 2300 receives the optimum elastic strength from the calculation device 1200. The adjustment device 2300 adjusts the elastic strength so that the elastic strength of the elastic orthotic device 2400 coincides with the received optimum elastic strength (Step S203).

In the foregoing, the elastic orthotic devices fitted to the lower limb, especially, to the hip joint and the ankle joint are described by way of example. However, without being limited thereto, any other parts may be assisted. For instance, it is also applicable to motion assistance for joints of an upper limb, a finger, and a waist portion.

Thus, according to this second example embodiment, the strength adjustment of the elastic orthotic device 2400 becomes even easier. This is because adjustment of the elastic strength of the elastic orthotic device 2400 is automatically carried out by a function of the adjustment device 2300 to thereby save time and effort required for manual adjustment.

Third Example Embodiment

Next, a third example embodiment of the present invention will be described in detail with reference to the drawings.

Explanation of Configuration

Figure 8:
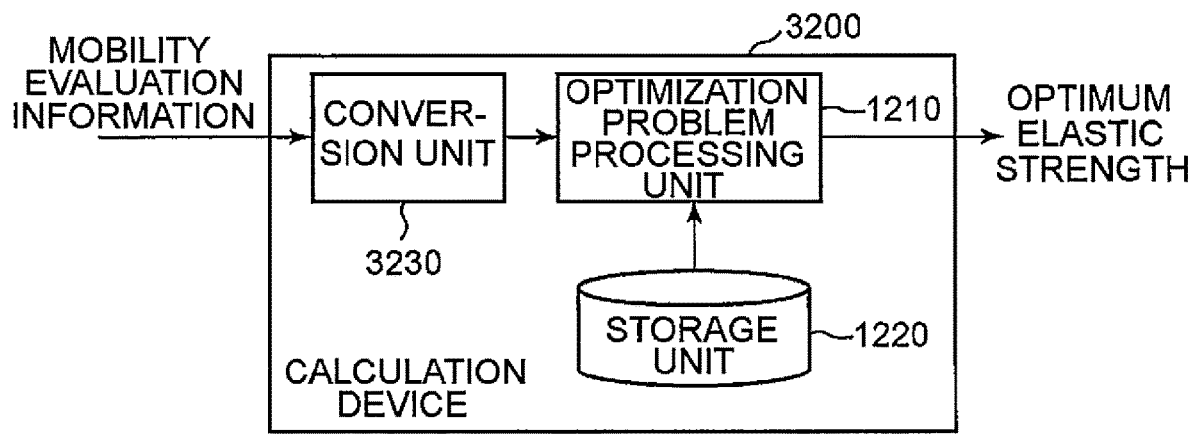
FIG. 8 is a block diagram for illustrating an example of a configuration of a calculation device according to a third example embodiment of the present invention.

FIG. 8 is a block diagram for illustrating an example of a configuration of a calculation device 3200 according to the third example embodiment in the present invention. As illustrated in FIG. 8, the calculation device 3200 comprises the optimization problem processing unit 1210, the storage unit 1220, and a conversion unit 3230.

The optimization problem processing unit 1210 and the storage unit 1220 carry out operations same as those of the calculation device 1200 illustrated in FIG. 2.

The conversion unit 3230 is supplied with mobility evaluation information. Herein, the "mobility evaluation information" is an index quantitatively indicating a mobility of the orthotics user. By way of example, there are a TUG (Timed Up and Go) test, a six-minute walking test, one-leg standing time with eyes open, and so on. The conversion unit 3230 converts the supplied mobility evaluation information into a kinematic constraint condition which is supplied to the optimization problem processing unit 1210.

As one example of calculation for converting the mobility evaluation information into the kinematic constraint condition, there is a two-variable linear function represented by the following Math. 6 using the TUG and the one-leg standing time with eyes open as variables. It is to be noted that the TUG is a time required for a person to stand up from a chair, walk a distance of 3 m at a comfortable pace, turn back, and takes a seat. The one-leg standing time with eyes open is a time from starting one-leg standing with eyes open to losing balance.

$$\overline{MVC_m} = \alpha \times TUG + \beta \times \text{one-leg standing time with eyes open} + \gamma \quad [\text{Math. 6}]$$

where $$\overline{MVC_m} \quad [\text{Math. 7}]$$

is the limit value of the maximum muscle activity amount of the muscle m as described above. In addition, $\alpha$, $\beta$, and $\gamma$ are coefficients. The respective coefficients are obtained by using data which are obtained by carrying out, for a sufficiently large number of people, experiments for measuring a set of the TUG, the one-leg standing time with eyes open, and the maximum muscle activity amount, and by performing a multiple regression analysis using the maximum muscle activity amount as an objective variable and using the TUG and the one-leg standing time with eyes open as explanatory variables.

As another example of the mobility evaluation information, there is a MMT (Manual Muscle Test). The MMT is a test for evaluating a muscle weakness condition and takes discrete values of six grades between 0 and 5, both inclusive. An examination method comprises the steps of manually applying, by an examiner (doctor or physical therapist), resistance in an expansion direction in a state where an examinee contracts a muscle or a group of muscles as a target, and of evaluating contraction retention ability of the muscle or the group of muscles. There is a linear function represented by the following Math. 8 using the MMT as an explanatory variable:

$$\overline{MVC_j} = \alpha \times MMT + \beta \qquad \text{[Math. 8]}$$

Herein, $\alpha$ and $\beta$ are coefficients. The respective coefficients are obtained by using data which are obtained by carrying out, for a sufficiently large number of people, experiments for measuring a set of the MMT and the maximum muscle activity amount and by performing a single regression analysis using the maximum muscle activity amount as an objective variable and using the MMT as explanatory variables.

Explanation of Operation

Next, an operation of the calculation device 3200 of this third example embodiment will be described with reference to the drawings.

Figure 9:
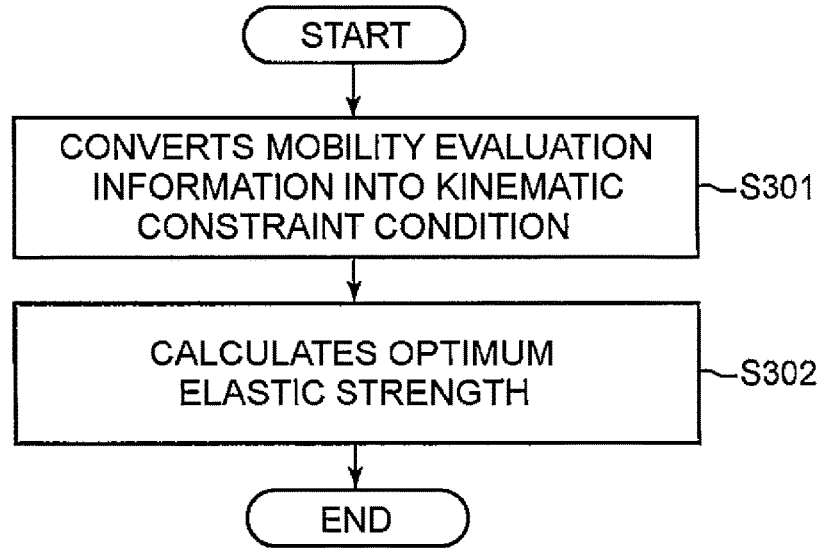
FIG. 9 is a flow chart for representing an example of an operation of the calculation device according to the third example embodiment of the present invention.

FIG. 9 is a flow chart for representing an example of the operation of the calculation device 3200 according to this third example embodiment.

First, the conversion unit 3230 receives the mobility evaluation information from the input device 1100. The conversion unit 3230 converts the mobility evaluation information into the kinematic constraint condition (Step S301). Then, the conversion unit 3230 supplies the converted kinematic constraint condition to the optimization problem processing unit 1210.

The optimization problem processing unit 1210 receives the kinematic constraint condition from the conversion unit 3230. The optimization problem processing unit 1210 calculates the optimum elastic strength using the received kinematic constraint condition as described above (Step S302).

According to this third example embodiment, the mobility evaluation information can be inputted instead of the kinematic constraint condition. It is therefore possible to directly use values of examination items which are generally performed in rehabilitation and this exhibits an effect of improving convenience of the system.

It is to be noted that each part of the calculation device 3200 may be implemented by using a combination of hardware and software. Ina form in which the hardware and the software are combined, the respective parts are implemented as various kinds of means by developing an optimum elastic strength calculation program in a RAM (random access memory) and making hardware such as a control unit (a CPU (central processing unit)) operate based on the optimum elastic strength calculation program. The optimum elastic strength calculation program may be recorded in a recording medium to be distributed. The optimum elastic strength calculation program recorded in the recording medium is read into a memory via a wire, wirelessly, or via the recording medium itself to operate the control unit and so on. By way of example, the recording medium may be an optical disc, a magnetic disk, a semiconductor memory device, a hard disk, or the like.

Explaining the above-mentioned third example embodiment with a different expression, it is possible to implement the third example embodiment by making a computer to be operated as the calculation device 3200 act as the optimization problem processing unit 1210, the storage unit 1220, and the conversion unit 3230 according to the optimum elastic strength calculation program developed in the RAM.

Modification of Third Example Embodiment

The optimization problem processing unit 1210 of the calculation device 3200 may be further supplied with rehabilitation plan information in addition to the kinematic constraint condition.

Herein, the "rehabilitation plan information" is a plan which is set in accordance with a progress stage of the rehabilitation. For instance, a table is conceivable in which the mobility evaluation information of a rehabilitation patient is associated with an optimization evaluation index corresponding thereto. Taking walking rehabilitation, for example, in an initial stage of the rehabilitation (mobility evaluation index value is low), it is important that an excessive load is not imposed on the joint. It is therefore supposed that the evaluation index for minimizing the maximum joint moment is suitable. However, in a stage where the mobility evaluation index value is improved with a progress of the rehabilitation, the evaluation index for maximizing the walking speed is more suitable for the purpose of independence in daily life.

The optimization problem processing unit of this modification acquires, with reference to the input rehabilitation plan information, the optimization evaluation index corresponding to the current mobility evaluation information of a rehabilitation patient to calculate the optimum elastic strength.

In this manner, the optimum elastic strength according to the rehabilitation stage is calculated, and this exhibits an effect of further improving convenience of the system.

Although the example embodiments of this invention has been described above with reference to the drawings, it is to be noted that those skilled in the art could use other similar example embodiments and could appropriately carry out alternations or additions of the embodiments without departing from this invention.

A part or a whole of the example embodiments described above may be described as, but not limited to, the following supplementary notes.

(Supplementary Note 1)

An optimum elastic strength calculation device comprising:
 a storage unit configured to preliminarily store an elastic strength and kinematic property obtained through experiments in a state where an elastic orthotic device for assisting an action of an orthotics user is worn on bodies of a plurality of people; and
 an optimization problem processing unit configured to calculate an optimum elastic strength of the elastic orthotic device based on a predetermined evaluation index using a kinematic constraint condition of the orthotics user and the elastic strength and kinematic property.

(Supplementary Note 2)

The optimum elastic strength calculation device according to Supplementary Note 1, wherein the elastic strength and kinematic property comprises a predictive value of a walking speed, a predictive value of a maximum bending angle of a joint, a predictive value of a maximum extension angle of the joint, a predictive value of a maximum joint moment of the joint, and a predictive value of a maximum muscle activity amount of a muscle which are obtained through the experiments in the state where the elastic orthotic device is worn on the bodies of the plurality of people.

(Supplementary Note 3)

The optimum elastic strength calculation device according to Supplementary Note 1 or 2, wherein the kinematic constraint condition comprises a kinematic condition to be satisfied by a pedestrian as the orthotics user during the action.

(Supplementary Note 4)

The optimum elastic strength calculation device according to any one of Supplementary Notes 1 to 3, wherein the predetermined evaluation index comprises one selected from the group consisting of a first index for maximizing the walking speed of the orthotics user, a second index for maximizing a range of joint motion, a third index for minimizing the maximum joint moment, and a fourth index obtained as a weighted average of the first through the third indexes.

(Supplementary Note 5)

An optimum elastic strength calculation system comprising:
 an input device configured to input a kinematic constraint condition of an orthotics user;
 the optimum elastic strength calculation device according to any one of Supplementary Notes 1 to 4; and
 a display device configured to output the optimum elastic strength.

(Supplementary Note 6)

A motion assistance system comprising:
 an elastic orthotics device which is configured to be worn on a body of an orthotics user to assist an action of the orthotics user;
 an input device configured to input a kinematic constraint condition of the orthotics user;
 the optimum elastic strength calculation device according to any one of Supplementary Notes 1 to 4; and
 an adjustment device configured to adjust, in response to the optimum elastic strength, an elastic strength of the elastic orthotic device.

(Supplementary Note 7)

An optimum elastic strength calculation method comprising:
 preliminarily storing, in a storage unit, an elastic strength and kinematic property which is obtained through experiments in a state where an elastic orthotic device for assisting an action of an orthotics user is worn on bodies of a plurality of people; and
 calculating, by an optimization problem processing unit, an optimum elastic strength of the elastic orthotic device based on a predetermined evaluation index using a kinematic constraint condition of the orthotics user and the elastic strength and kinematic property.

(Supplementary Note 8)

The optimum elastic strength calculation method according to Supplementary Note 7, wherein the elastic strength and kinematic property comprises a predictive value of a walking speed, a predictive value of a maximum bending angle of a joint, a predictive value of a maximum extension angle of the joint, a predictive value of a maximum joint moment of the joint, and a predictive value of a maximum muscle activity amount of a muscle which are obtained through the experiments in the state where the elastic orthotic device is worn on the bodies of the plurality of people.

(Supplementary Note 9)

The optimum elastic strength calculation method according to Supplementary Note 7 or 8, wherein the kinematic constraint condition comprises a kinematic condition to be satisfied by a pedestrian as the orthotics user during the action.

(Supplementary Note 10)

The optimum elastic strength calculation method according to any one of Supplementary Notes 7 to 9, wherein the predetermined evaluation index comprises one selected from the group consisting of a first index for maximizing the walking speed of the orthotics user, a second index for maximizing a range of joint motion, a third index for minimizing the maximum joint moment, and a fourth index obtained as a weighted average of the first through the third indexes.

(Supplementary Note 11)

An optimum elastic strength calculation program recording medium for recording an optimum elastic strength calculation program to cause a computer to calculate an optimum elastic strength of an elastic orthotic device which is worn on a body of an orthotics user to assist an action of the orthotics user, wherein the optimum elastic strength calculation program causes the computer to execute:
 a step of preliminarily storing, in a storage unit, an elastic strength and kinematic property which is obtained through experiments in a state where the elastic orthotic device for assisting the action of the orthotics user is worn on bodies of a plurality of people; and
 an optimization problem processing step of calculating the optimum elastic strength of the elastic orthotic device based on a predetermined evaluation index using a kinematic constraint condition of the orthotics user and the elastic strength and kinematic property.

(Supplementary Note 12)

The optimum elastic strength calculation program recording medium according to Supplementary Note 11, wherein the elastic strength and kinematic property comprises a predictive value of a walking speed, a predictive value of a maximum bending angle of a joint, a predictive value of a maximum extension angle of the joint, a predictive value of a maximum joint moment of the joint, and a predictive value of a maximum muscle activity amount of a muscle which are obtained through the experiments in the state where the elastic orthotic device is worn on the bodies of the plurality of people.

(Supplementary Note 13)

The optimum elastic strength calculation program recording medium according to Supplementary Note 11 or 12, wherein the kinematic constraint condition comprises a kinematic condition to be satisfied by a pedestrian as the orthotics user during the action.

(Supplementary Note 14)

The optimum elastic strength calculation program recording medium according to any one of Supplementary Notes 11 to 13, wherein the predetermined evaluation index comprises one selected from the group consisting of a first index for maximizing the walking speed of the orthotics user, a second index for maximizing a range of joint motion, a third index for minimizing the maximum joint moment, and a fourth index obtained as a weighted average of the first through the third indexes.

(Supplementary Note 15)

An optimum elastic strength calculation device comprising:
 a storage unit configured to preliminarily store an elastic strength and kinematic property obtained through experiments in a state where an elastic orthotic device for assisting an action of an orthotics user is worn on bodies of a plurality of people;
a conversion unit configured to convert mobility evaluation information of the orthotics user into a kinematic constraint condition; and
an optimization problem processing unit configured to calculate an optimum elastic strength of the elastic orthotic device based on a predetermined evaluation index using the kinematic constraint condition and the elastic strength and kinematic property.

(Supplementary Note 16)

The optimum elastic strength calculation device according to Supplementary Note 15,
wherein the elastic strength and kinematic property comprises a predictive value of a walking speed, a predictive value of a maximum bending angle of a joint, a predictive value of a maximum extension angle of the joint, a predictive value of a maximum joint moment of the joint, and a predictive value of a maximum muscle activity amount of a muscle which are obtained through the experiments in the state where the elastic orthotic device is worn on the bodies of the plurality of people.

(Supplementary Note 17)

The optimum elastic strength calculation device according to Supplementary Note 15 or 16, wherein the mobility evaluation information comprises an index quantitatively indicating a mobility of the orthotics user.

(Supplementary Note 18)

The optimum elastic strength calculation device according to any one of Supplementary Notes 15 to 17, wherein the kinematic constraint condition comprises a kinematic condition to be satisfied by a pedestrian as the orthotics user during the action.

(Supplementary Note 19)

The optimum elastic strength calculation device according to any one of Supplementary Notes 15 to 18, wherein the predetermined evaluation index comprises one selected from the group consisting of a first index for maximizing the walking speed of the orthotics user, a second index for maximizing a range of joint motion, a third index for minimizing the maximum joint moment, and a fourth index obtained as a weighted average of the first through the third indexes.

(Supplementary Note 20)

An optimum elastic strength calculation system comprising:
an input device configured to input mobility evaluation information of an orthotics user;
the optimum elastic strength calculation device according to any one of Supplementary Notes 15 to 19; and
a display device configured to output the optimum elastic strength.

(Supplementary Note 21)

A motion assistance system comprising:
an elastic orthotic device which is configured to be worn on a body of an orthotics user to assist an action of the orthotics user;
an input device configured to input mobility evaluation information of the orthotics user,
the optimum elastic strength calculation device according to any one of Supplementary Note 15 to 19; and
an adjustment device configured to adjust, in response to the optimum elastic strength, an elastic strength of the elastic orthotic device.

(Supplementary Note 22)

An optimum elastic strength calculation method comprising:
preliminarily storing, in a storage unit, an elastic strength and kinematic property which is obtained through experiments in a state where an elastic orthotic device for assisting an action of an orthotics user is worn on bodies of a plurality of people;
converting, by a conversion unit, mobility evaluation information of the orthotics user into a kinematic constraint condition; and
calculating, by an optimization problem processing unit, an optimum elastic strength of the elastic orthotic device based on a predetermined evaluation index using the kinematic constraint condition and the elastic strength and kinematic property.

(Supplementary Note 23)

The optimum elastic strength calculation method according to Supplementary Note 22, wherein the elastic strength and kinematic property comprises a predictive value of a walking speed, a predictive value of a maximum bending angle of a joint, a predictive value of a maximum extension angle of the joint, a predictive value of a maximum joint moment of the joint, and a predictive value of a maximum muscle activity amount of a muscle which are obtained through the experiments in the state where the elastic orthotic device is worn on the bodies of the plurality of people.

(Supplementary Note 24)

The optimum elastic strength calculation method according to Supplementary Note 22 or 23, wherein the mobility evaluation information comprises an index quantitatively indicating a mobility of the orthotics user.

(Supplementary Note 25)

The optimum elastic strength calculation method according to any one of Supplementary Notes 22 to 24, wherein the kinematic constraint condition comprises a kinematic condition to be satisfied by a pedestrian as the orthotics user during the action.

(Supplementary Note 26)

The optimum elastic strength calculation method according to any one of Supplementary Notes 22 to 25, wherein the predetermined evaluation index comprises one selected from the group consisting of a first index for maximizing the walking speed of the orthotics user, a second index for maximizing a range of joint motion, a third index for minimizing the maximum joint moment, and a fourth index obtained as a weighted average of the first through the third indexes.

(Supplementary Note 27)

An optimum elastic strength calculation program recording medium for recording an optimum elastic strength calculation program to cause a computer to calculate an optimum elastic strength of an elastic orthotic device which is worn on a body of an orthotics user to assist an action of the orthotics user, wherein the optimum elastic strength calculation program causes the computer to execute:
a step of preliminarily storing, in a storage unit, an elastic strength and kinematic property which is obtained through experiments in a state where the elastic orthotic device for assisting the action of the orthotics user is worn on bodies of a plurality of people;
a conversion step of converting mobility evaluation information of the orthotics user into a kinematic constraint condition; and
an optimization problem processing step of calculating the optimum elastic strength of the elastic orthotic device based on a predetermined evaluation index using the kinematic constraint condition and the elastic strength and kinematic property.

(Supplementary Note 28)

The optimum elastic strength calculation program recording medium according to Supplementary Note 27, wherein the elastic strength and kinematic property comprises a predictive value of a walking speed, a predictive value of a maximum bending angle of a joint, a predictive value of a maximum extension angle of the joint, a predictive value of a maximum joint moment of the joint, and a predictive value of a maximum muscle activity amount of a muscle which are obtained through the experiments in the state where the elastic orthotic device is worn on the bodies of the plurality of people.

(Supplementary Note 29)

The optimum elastic strength calculation program recording medium according to Supplementary Note 27 or 28,
wherein the mobility evaluation information comprises an index quantitatively indicating a mobility of the orthotics user (Supplementary Note 30)

The optimum elastic strength calculation program recording medium according to any one of Supplementary Notes 27 to 29, wherein the kinematic constraint condition comprises a kinematic condition to be satisfied by a pedestrian as the orthotics user during the action.

(Supplementary Note 31)

The optimum elastic strength calculation program recording medium according to any one of Supplementary Notes 27 to 30, wherein the predetermined evaluation index comprises one selected from the group consisting of a first index for maximizing the walking speed of the orthotics user, a second index for maximizing a range of joint motion, a third index for minimizing the maximum joint moment, and a fourth index obtained as a weighted average of the first through the third indexes.

While the invention has been particularly shown and described with reference to the example embodiments thereof, the invention is not limited to these embodiments described above. It will be understood by those skilled in the art that various changes in form and details may be made therein within the scope of the present invention.

INDUSTRIAL APPLICABILITY

The present invention is applicable to, as a practical example, walking rehabilitation of a hemiplegia patient and an aged person. Furthermore, the motion assistance system of this invention is also applicable to correction of walking and running forms of an able-bodied person and an athlete.

REFERENCE SIGNS LIST 1 optimum elastic strength calculation system
2 motion assistance system
10 orthotics user
20 terminal
100 first motion assistance device
112 first elastic body holding unit
113 first assistance unit
114 first shaft
115 waist belt
116 knee belt
120 elastic body (spring)
121 pressing force reception unit
123 female screw
200 second motion assistance device
212 second elastic body holding unit
213 second assistance unit
214 second shaft
215 shank belt
216 sole plate
1100 input device
1200 calculation device (optimum elastic strength calculation device
1210 optimization problem processing unit
1220 storage unit
1300 display device
2300 adjustment device
2300a first adjustment device
2300b second adjustment device
2310 servomotor
2320 shaft
2330 shaft
2340 fixing member
2350 gear
2360 gear
2370 male screw
2400 elastic orthotic device
2400a first elastic orthotic device
2400b second elastic orthotic device
3200 calculation device (optimum elastic strength calculation device)
3230 conversion unit

The invention claimed is:

1. An optimum elastic strength calculation device comprising:
a storage unit configured to preliminarily store an elastic strength and kinematic property obtained through experiments in a state where an elastic orthotic device for assisting an action of an orthotics user is worn on bodies of a plurality of people; and
an optimization problem processing unit configured to calculate an optimum elastic strength of the elastic orthotic device based on a predetermined evaluation index using a kinematic constraint condition of the orthotics user and the elastic strength and kinematic property,
wherein the elastic strength and kinematic property comprises a predictive value of a walking speed, a predictive value of a maximum bending angle of a joint, a predictive value of a maximum extension angle of the joint, a predictive value of a maximum joint moment of the joint, and a predictive value of a maximum muscle activity amount of a muscle which are obtained through the experiments in the state where the elastic orthotic device is worn on the bodies of the plurality of people.

2. The optimum elastic strength calculation device as claimed in claim 1, wherein the kinematic constraint condition comprises a kinematic condition to be satisfied by a pedestrian as the orthotics user during the action.

3. The optimum elastic strength calculation device as claimed in claim 1, wherein the predetermined evaluation index comprises one selected from the group consisting of a first index for maximizing the walking speed of the orthotics user, a second index for maximizing a range of joint motion, a third index for minimizing the maximum joint moment, and a fourth index obtained as a weighted average of the first through the third indexes.

4. An optimum elastic strength calculation system comprising:
an input device configured to input a kinematic constraint condition of an orthotics user;

the optimum elastic strength calculation device claimed in claim 1; and a display device configured to output the optimum elastic strength.

5. A motion assistance system comprising:

an elastic orthotics device which is configured to be worn on a body of an orthotics user to assist an action of the orthotics user;

an input device configured to input a kinematic constraint condition of the orthotics user;

the optimum elastic strength calculation device claimed in claim 1; and an adjustment device configured to adjust, in response to the optimum elastic strength, an elastic strength of the elastic orthotic device.

6. An optimum elastic strength calculating method comprising:

preliminarily storing, in a storage unit, an elastic strength and kinematic property which is obtained through experiments in a state where an elastic orthotic device for assisting an action of an orthotics user is worn on bodies of a plurality of people; and calculating, by an optimization problem processing unit, an optimum elastic strength of the elastic orthotic device based on a predetermined evaluation index using a kinematic constraint condition of the orthotics user and the elastic strength and kinematic property, wherein the elastic strength and kinematic property comprises a predictive value of a walking speed, a predictive value of a maximum bending angle of a joint, a predictive value of a maximum extension angle of the joint, a predictive value of a maximum joint moment of the joint, and a predictive value of a maximum muscle activity amount of a muscle which are obtained through the experiments in the state where the elastic orthotic device is worn on the bodies of the plurality of people.

7. The optimum elastic strength calculation method as claimed in claim 6, wherein the kinematic constraint condition comprises a kinematic condition to be satisfied by a pedestrian as the orthotics user during the action.

8. The optimum elastic strength calculation method as claimed in claim 6, wherein the predetermined evaluation index comprises one selected from the group consisting of a first index for maximizing the walking speed of the orthotics user, a second index for maximizing a range of joint motion, a third index for minimizing the maximum joint moment, and a fourth index obtained as a weighted average of the first through the third indexes.

9. A non-transitory optimum elastic strength calculation program recording medium for recording an optimum elastic strength calculation program to cause a computer to calculate an optimum elastic strength of an elastic orthotic device which is worn on a body of an orthotics user to assist an action of the orthotics user, wherein the optimum elastic strength calculation program causes the computer to execute:

an operation of preliminarily storing, in a storage unit, an elastic strength and kinematic property which is obtained through experiments in a state where the elastic orthotic device for assisting the action of the orthotics user is worn on bodies of a plurality of people; and an optimization problem processing operation of calculating the optimum elastic strength of the elastic orthotic device based on a predetermined evaluation index using a kinematic constraint condition of the orthotics user and the elastic strength and kinematic property, wherein the elastic strength and kinematic property comprises a predictive value of a walking speed, a predictive value of a maximum bending angle of a joint, a predictive value of a maximum extension angle of the joint, a predictive value of a maximum joint moment of the joint, and a predictive value of a maximum muscle activity amount of a muscle which are obtained through the experiments in the state where the elastic orthotic device is worn on the bodies of the plurality of people.

10. The non-transitory optimum elastic strength calculation program recording medium as claimed in claim 9, wherein the kinematic constraint condition comprises a kinematic condition to be satisfied by a pedestrian as the orthotics user during the action.

11. The non-transitory optimum elastic strength calculation program recording medium as claimed in claim 9, wherein the predetermined evaluation index comprises one selected from the group consisting of a first index for maximizing the walking speed of the orthotics user, a second index for maximizing a range of joint motion, a third index for minimizing the maximum joint moment, and a fourth index obtained as a weighted average of the first through the third indexes.

* * * * *